US012616367B2

(12) United States Patent
Kano

(10) Patent No.: US 12,616,367 B2
(45) Date of Patent: May 5, 2026

(54) OPTICAL SYSTEM AND INSPECTION APPARATUS

(71) Applicant: CANON KABUSHIKI KAISHA, Tokyo (JP)

(72) Inventor: Hiroto Kano, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 555 days.

(21) Appl. No.: 18/166,861

(22) Filed: Feb. 9, 2023

(65) Prior Publication Data

US 2023/0266568 A1     Aug. 24, 2023

(30) Foreign Application Priority Data

Feb. 18, 2022    (JP) ................................. 2022-023869

(51) Int. Cl.
| | |
|---|---|
| *A61B 3/113* | (2006.01) |
| *A61B 3/00* | (2006.01) |
| *A61B 3/14* | (2006.01) |
| *G02B 13/00* | (2006.01) |
| *G02B 27/00* | (2006.01) |
| *G06T 7/70* | (2017.01) |
| *A61B 3/12* | (2006.01) |

(52) U.S. Cl.
CPC ............ *A61B 3/113* (2013.01); *A61B 3/0008* (2013.01); *A61B 3/14* (2013.01); *G02B 13/0065* (2013.01); *G02B 27/0093* (2013.01); *G06T 7/70* (2017.01); *A61B 3/12* (2013.01)

(58) Field of Classification Search
CPC ....... A61B 3/0091; A61B 3/14; A61B 3/0008; A61B 3/12; A61B 3/113; A61B 5/163; G02B 27/0093; G06F 3/013; G06T 2207/30041
See application file for complete search history.

(56) References Cited

U.S. PATENT DOCUMENTS

| | | | |
|---|---|---|---|
| 10,188,293 B2 | 1/2019 | Winsor | |
| 2012/0229768 A1* | 9/2012 | Gramatikov ........... | A61B 3/113 351/215 |
| 2016/0174832 A1* | 6/2016 | Winsor .................... | A61B 3/14 351/245 |
| 2017/0236337 A1* | 8/2017 | Devries .................. | G06T 19/20 345/419 |

FOREIGN PATENT DOCUMENTS

| | | | | |
|---|---|---|---|---|
| CN | 107290917 A | * | 10/2017 | ......... G03B 21/2053 |
| EP | 3440990 A1 | * | 2/2019 | ............. A61B 3/156 |

* cited by examiner

*Primary Examiner* — Balram T Parbadia
*Assistant Examiner* — Alex Park Rickel
(74) *Attorney, Agent, or Firm* — Canon U.S.A., Inc. IP Division

(57) ABSTRACT

An optical system is configured to guide light from a light source to a first target and a second target, and to guide first reflected light from the first target and second reflected light from the second target to an image sensor. The optical system includes a first optical element having a conical surface. An intermediate image is formed between the first optical element and each of the first target and the second target. The first reflected light and the second reflected light are guided to an imaging plane of the image sensor such that at least part of the first reflected light and part of the second reflected light overlap each other on the imaging plane.

14 Claims, 6 Drawing Sheets

ARRANGEMENT
DIRECTION OF
BOTH EYES

OPTICAL SYSTEM AND INSPECTION APPARATUS

BACKGROUND

Technical Field

One of the aspects of the disclosure relates to an optical system and an inspection apparatus.

Description of the Related Art

It is known that the fovea (a dent or depression at the center of the macula of a retina in an eye) is a place where the best vision is obtained because the retinal cones are particularly concentrated this neurosensory region. It is also known that a position where a test subject (test person) is gazing for visual fixation is measurable by detecting the birefringence states of neurons around the fovea. U.S. Pat. No. 10,188,293 discloses an inspection apparatus that includes a projection apparatus configured to project light onto the retina in the eye, and a light detector (sensor) configured to receive light reflected on the retina. Alight receiving surface of the light detector disclosed in U.S. Pat. No. 10,188,293 is located at a position conjugate with the retina and receives the light reflected on the retina of the eye.

The inspection apparatus disclosed in U.S. Pat. No. 10,188,293 includes lenses disposed near an intermediate image in order to optically separate lights reflected on the retinas of both eyes. However, the optical system of the projection apparatus and the optical system that guides the reflected light to the optical detector are different, and thus this configuration needs to suppress a relative positional shift between the optical system of the projection apparatus and the optical system that guides the reflected light in order to prevent the detection accuracy from lowering. As a result, the inspection apparatus becomes complicated and large.

SUMMARY

One of the aspects of the disclosure provides an optical system and inspection apparatus, each of which is small and has a simple configuration.

An optical system according to one aspect of the disclosure is configured to guide light from a light source to a first target and a second target, and to guide first reflected light from the first target and second reflected light from the second target to an image sensor. The optical system includes a first optical element having a conical surface. An intermediate image is formed between the first optical element and each of the first target and the second target. The first reflected light and the second reflected light are guided to an imaging plane of the image sensor such that at least part of the first reflected light and part of the second reflected light overlap each other on the imaging plane. An inspection apparatus having the above optical system also constitutes another aspect of the disclosure.

Further features of the disclosure will become apparent from the following description of embodiments with reference to the attached drawings.

DESCRIPTION OF THE EMBODIMENTS

Referring now to the accompanying drawings, a detailed description will be given of embodiments according to the disclosure. An optical system according to each example is used, for example, as a projection optical system for an inspection apparatus (fixation measuring apparatus) that inspects a position where an eye of a subject is gazing (fixation state). As used herein, the term "gazing" describes an action to look steadily and intently at something or someone for at least a predetermined amount of time. A detailed description will be given of the configuration of the optical system according to each example.

EXAMPLE 1

Figure 1:
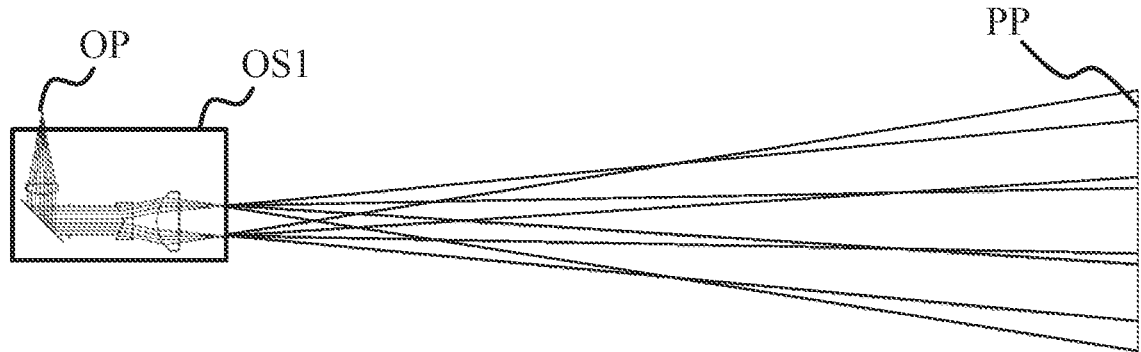
FIG. 1 is an optical path diagram of an optical system according to Example 1.
Figure 2:
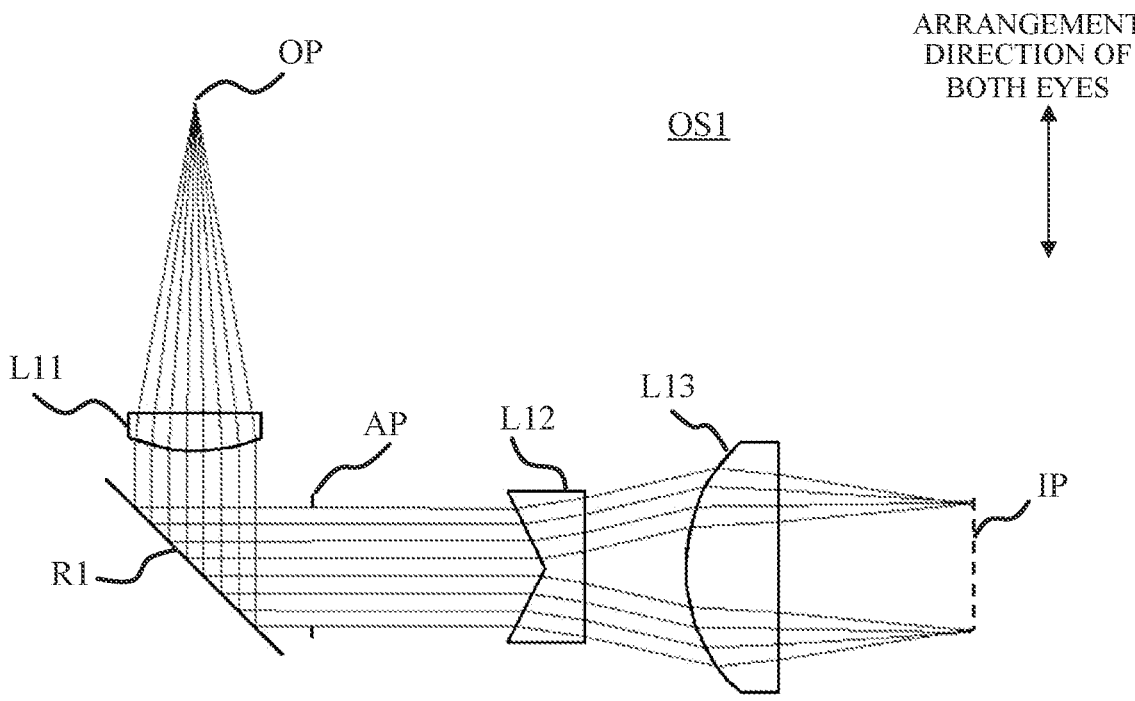
FIG. 2 is a sectional view of the optical system according to Example 1.

Referring now to FIGS. 1 and 2, a description will be given of an optical system OS1 according to Example 1. FIG. 1 is an optical path diagram of the optical system OS1 (optical path diagram from a reduction plane (object or light emitting plane) OP to an enlargement plane (target plane, projection plane) PP via the optical system OS1). FIG. 2 is a sectional view of the optical system OS1.

The optical system OS1 includes, in order from the reduction plane (light emitting plane) OP to the enlargement plane PP, a lens L11, a reflective surface R1, a diaphragm (optical diaphragm, aperture stop) AP, a lens L12, and a lens L13. Light from the reduction plane OP is collimated by the lens L11, and then separated radially by a conical surface of the lens L12 to form a ring-shaped beam. A ring-shaped intermediate image IP is formed by the lens L13. The ring-shaped intermediate image IP enters the enlargement plane PP, that is, a pupil or retina (fundus) of an eye. A light source such as a laser diode that emits light is disposed in the reduction plane OP. The light source may use near-infrared or infrared wavelengths to reduce damage to the retina. The lens L12 is a conical lens (first optical element having a conical surface) such as an axicon lens. The reflective surface R1 includes a half-mirror, a polarization beam splitter, or the like. An angle (reflection angle) of the reflective surface R1 is not limited to an angle illustrated in FIG. 2.

In this embodiment, the light from the lens L11 is reflected on the reflective surface R1 and enters the lens L12, but the configuration is not limited to this example. For example, the light from the lens L11 may be directly introduced to the lens L12 without passing through the reflective surface R1. In this case, a prism (separation surface) may be disposed which separates the reflected light from the retina and guides it to the detector (see "Imaging Unit" in FIG. 10). This is similarly applicable to each example described below.

This embodiment uses a concave axicon lens for the lens L12. Using a concave axicon lens can advantageously make short the focal length of the lens L13, and can shorten the optical path and improve the diffusing performance to the enlargement plane.

The diaphragm AP may have a rectangular or elliptical aperture. The longitudinal direction of the aperture may be a lateral direction with respect to the subject (direction from an arbitrary point on a first target (left eyeball) to an arbitrary point on a second target (right eyeball)). This arrangement can significantly reduce the size of the optical system OS1. Assume that the vertical direction in FIG. 2 is an arrangement direction of both eyes. Then, the diaphragm AP has an aperture that is longer in the vertical direction than in the depth direction so that the vertical direction is the longitudinal direction.

Figure 3:
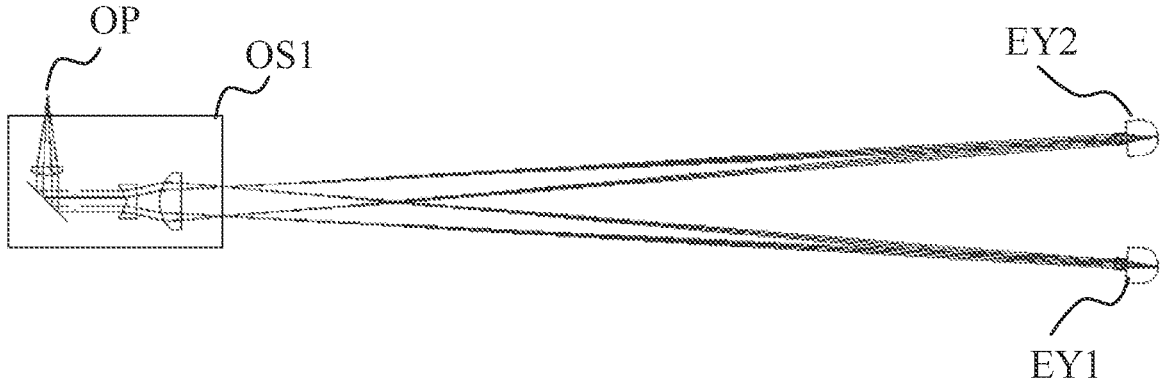
FIG. 3 is an optical path diagram to both eyes via the optical system according to Example 1.
Figure 4:
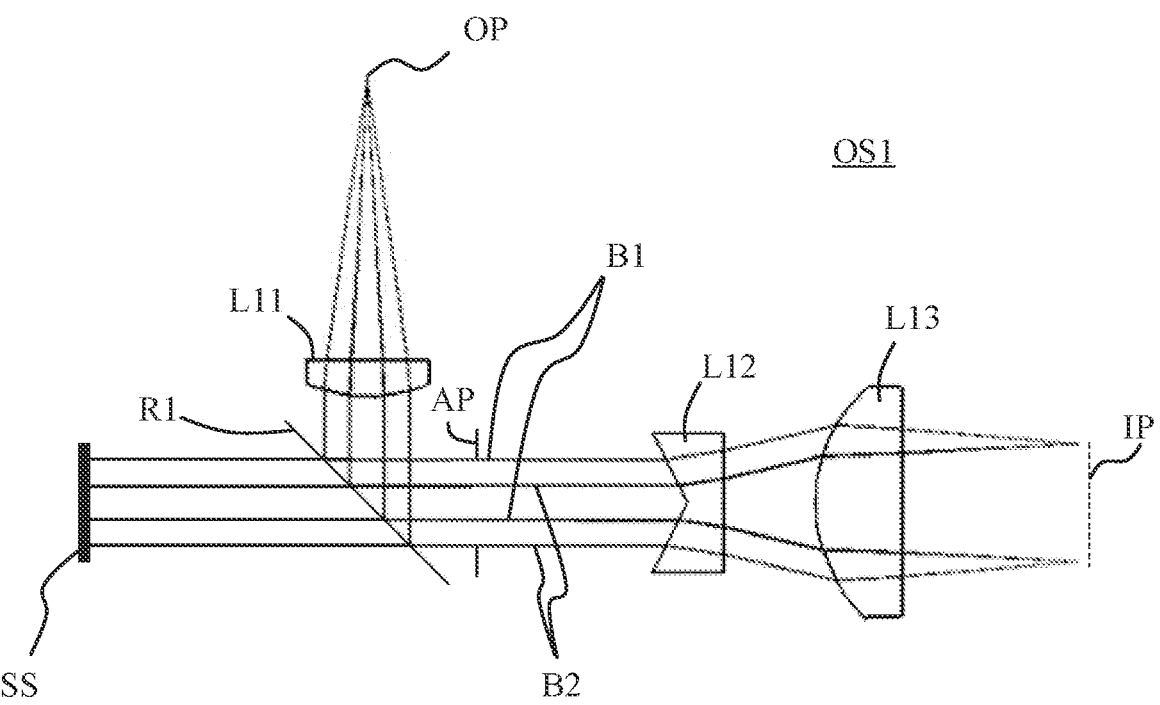
FIG. 4 is a sectional view of the optical system and detector according to Example 1.

Referring now to FIGS. 3 and 4, a description will be given of a method of detecting light projected onto the retinas in both eyes of the subject by the optical system OS1. FIG. 3 is an optical path diagram from the reduction plane OP to both eyes (eyes EY1 and EY2) of the subject located on the enlargement plane PP via the optical system OS1. FIG. 4 is a sectional view of the optical system OS1 and the detector (imaging unit) in FIG. 3.

As illustrated in FIGS. 3 and 4, reflected light (first reflected light) B1 from the retina in the eye (first target) EY1, reflected light (second reflected light) B2 from the eye (second target) EY2 are spatially separated. The reflected lights B1 and B2 are acquired after the subject views the intermediate image IP with the eyes EY1 and EY2. Therefore, it is possible to acquire sections of the reflected lights B1 and B2, that is, to separate and detect the lights from the retinas in the eyes EY1 and EY. As illustrated in FIG. 4, an image sensor SS is used as a detector configured to detect the reflected lights B1 and B2. The image sensor SS includes a light receiving surface (imaging plane) such as a Charge Coupled Device (CCD) sensor or a Complementary Metal Oxide Semiconductor (CMOS) sensor. The image sensor SS receives the lights B1 and B2 reflected on the eyes EY1 and EY2 that are located at positions conjugate to the intermediate image IP, respectively. The image sensor SS is disposed at a position that is not conjugated with the eye EY1 or the eye EY2. Each pixel of the image sensor SS may be able to obtain information (polarization information) on the polarization directions (polarization states) of the reflected lights B1 and B2 obtained based on the output of the image sensor SS. This configuration can detect the fixation state of each of the eyes EY1 and EY2.

The optical system OS1 guides the light from the light source to the eyes EY1 and EY2, and guides the reflected light B1 from the eye EY1 and the reflected light B2 from the eye EY2 to the image sensor SS. The optical system OS1 further includes the lens L12 having the conical surface, forms the intermediate image IP between the lens L12 and each of the eyes EY1 and EY2, and guides the reflected lights B1 and B2 to the imaging plane so that part of the reflected light B1 and part of the reflected light B2 overlap each other on the imaging plane of the image sensor SS. That is, since parts of the reflected lights B1 and B2 spatially overlap each other, a calculating unit 104 (see FIG. 10) is used to separately calculate the reflected lights B1 and B2 from the eyes EY1 and EY2. That is, the calculating unit 104 may separate the first image data corresponding to the reflected light B1 and output from the image sensor SS and the second image data corresponding to the reflected light B2 and output from the image sensor SS. The calculating unit 104 may separate the first image data and the second image data based on the polarization state of each of the reflected lights B1 and B2. Since it is unnecessary to optically separate the reflected lights B1 and B2 from the retinas in both eyes, the optical system OS1 can be made simple and small.

The optical system OS1 includes a projection optical system that guides light to the first and second targets, and an imaging optical system that guides the reflected lights B1 and B2 to the image sensor SS. In this embodiment, the projection optical system includes the lens L11, the reflective surface R1, the diaphragm AP, the lens L12, and the lens L13. The imaging optical system includes the lens L13, the lens L12, and the diaphragm AP. The lens L12 constitutes a part of the projection optical system and a part of the imaging optical system.

In this embodiment, to achieve one more of the above-described advantageous effects, one or more mathematical inequalities are satisfied. First, the following inequality may be satisfied:

$$1.8 \leq Fo \times \beta \leq 7.0 \tag{1}$$

where Fo is a target-side effective F-number (an F-number on the target side (enlargement, target, or projection plane side)) in the longitudinal direction of the optical system (direction from the first target to the second target), and $\beta$ is a magnification.

Inequality (1) defines a spatial range for simultaneous binocular imaging. In a case where the value is lower than the lower limit of inequality (1), the optical system OS1 and the inspection apparatus become larger and the assembly performance deteriorates. On the other hand, in a case where the value is higher than the upper limit of inequality (1), it becomes difficult to set a positional relationship between both eyes and the inspection apparatus that includes the optical system OS1, and the measurement accuracy deteriorates.

Inequality (1) may be replaced with the following inequality (1a):

$$2.0 \leq Fo \times \beta \leq 6.0 \tag{1a}$$

Inequality (1a) may be replaced with the following inequality (1b):

$$2.2 \leq Fo \times \beta \leq 5.0 \tag{1b}$$

In this embodiment, the following inequality (2) may be satisfied:

$$20 \leq L \times \beta / (2 \times Fo) \tag{2}$$

where L is the shortest distance from the intermediate image IP to the enlargement plane PP.

Inequality (2) defines a positional relationship for simultaneous imaging of both eyes. In a case where the value is lower than the lower limit of inequality (2), the optical system OS1 and the inspection apparatus become larger, and the assembly performance deteriorates.

Inequality (2) may be replaced with the following inequality (2a):

$$25 \leq L \times \beta / (2 \times Fo) \leq 100 \tag{2a}$$

In a case where the value is higher than the upper limit of inequality (2a), it becomes difficult to set the positional relationship between both eyes and the inspection apparatus that includes the optical system OS1, and the measurement accuracy deteriorates.

Inequality (2a) may be replaced with the following inequality (2b):

$$30 \leq L \times \beta/(2 \times Fo) \leq 95 \qquad (2b)$$

The inequalities (1), (1a), (1b), (2), (2a), and (2b) may be satisfied in each example described below.

Figure 5:
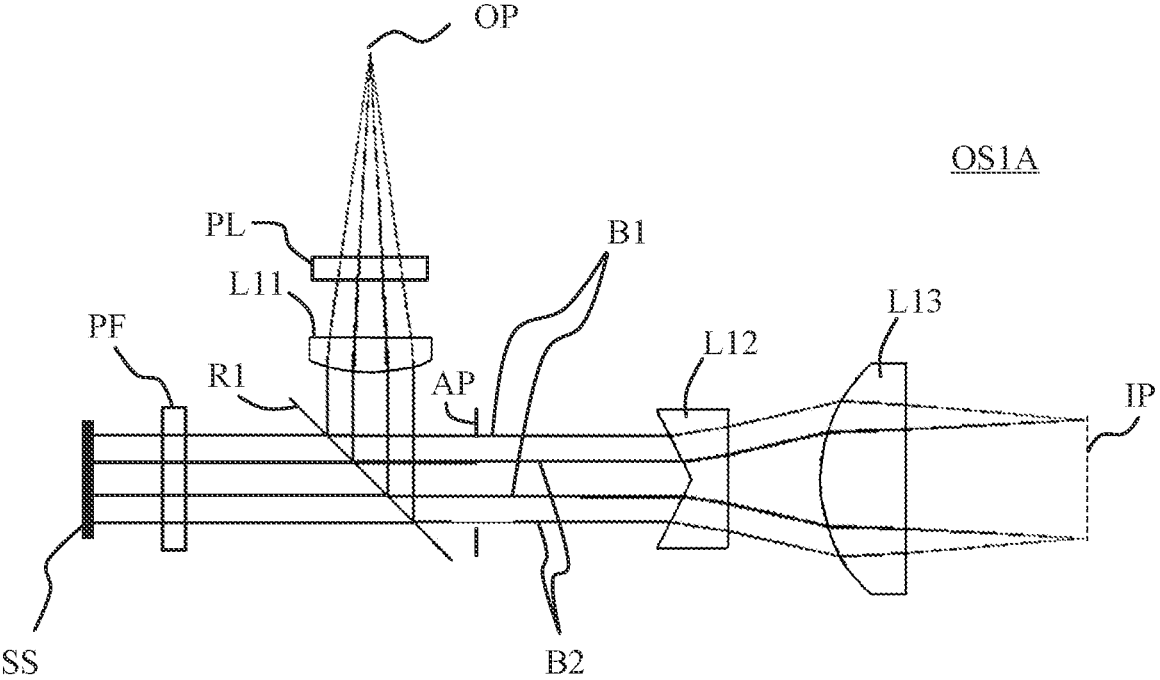
FIG. 5 is a sectional view of an optical system according to a first variation of Example 1.

Referring now to FIG. 5, a description will be given of a first variation of this embodiment. FIG. 5 is a sectional view of an optical system OS1A according to the first variation. As illustrated in FIG. 5, the optical system OS1A includes a polarizer PL located near the reduction plane (object plane) OP, and a polarizing filter PF located near the image sensor SS and constituting part of the imaging optical system. The polarizer PL converts the light emitted from a light source at the reduction plane OP into circularly polarized light. The polarizing filter PF is a filter that transmits light having polarization only in a desired polarization direction. The polarizing filter PF is rotatable to switch the polarization direction of the polarizing filter PF. That is, the polarizing filter PF serves as a light shielding unit that shields part of at least one of the reflected light B1 and the reflected light B2 (shields reflected light different from the reflected light B1 or the reflected light B2) based on a polarization state of the reflected light B1 and the reflected light B2. The polarizer PL can reduce noises caused by reflections from optical elements and the cornea in the eye, and the polarizing filter PF enables the fixation state of each of the eyes EY1 and EY2 to be detected even if the image sensor SS does not include a configuration for acquiring the polarization direction.

Figure 6:
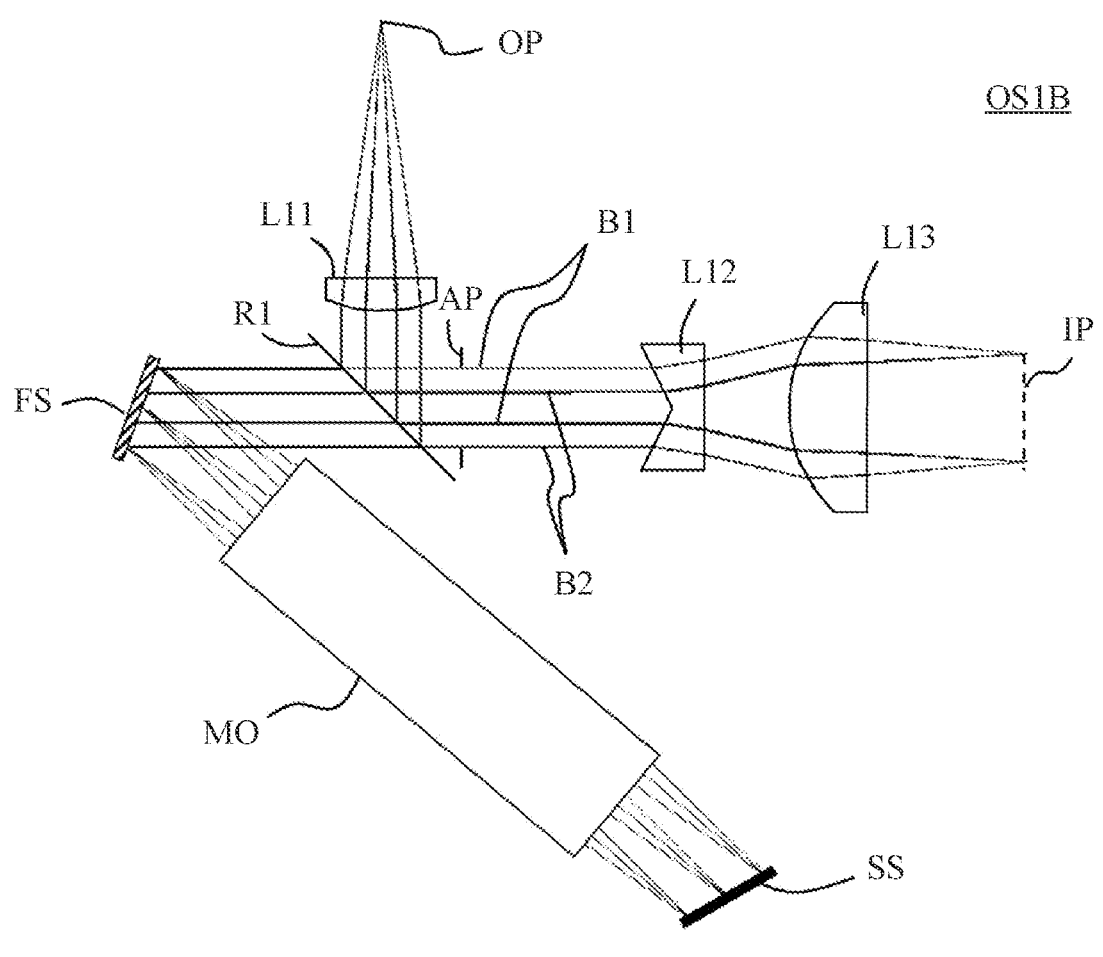
FIG. 6 is a sectional view of an optical system according to a second variation of Example 1.

Referring now to FIG. 6, a description will be given of a second variation of this embodiment. FIG. 6 is a sectional view of an optical system OS1B according to the second variation. As illustrated in FIG. 6, a diffusion screen FS that constitutes a part of the imaging optical system is disposed at a position corresponding to the location of the image sensor SS in FIG. 4. The reflected lights B1 and B2 are diffused by the diffusion screen FS, are guided to the image sensor SS via the optical system (optical system including a second optical element) MO, and captured by the image sensor SS as images. The diffusion screen FS may have a characteristic of diffusing the reflected lights B1 and B2 while maintaining the polarization state of each of the reflected lights B1 and B2. Forming an image on the image sensor SS via the diffusion screen FS can arbitrarily determine the magnification of the image using the optical system MO, and thereby improve the detection accuracy. In addition, since the diffusion screen FS and optical system MO make it unnecessary to directly introduce light onto the image sensor SS, damage to the image sensor SS can be suppressed. In FIG. 6, the diffusion screen FS is a reflective screen that reflects light, but a transmissive screen may be used instead. The angle of the diffusion screen FS, the arrangement angle of the optical system MO, the angle of the image sensor SS, and the like are not limited to those illustrated in FIG. 6.

Figure 7:
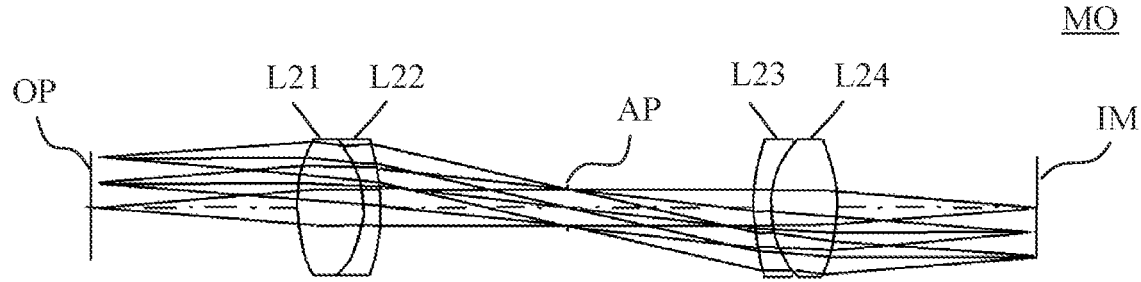
FIG. 7 is an example of a second optical system according to Example 1.

FIG. 7 is an example of an optical system MO. The diffusion screen FS is provided on the reduction plane OP, and a light receiving plane (imaging plane) of the image sensor SS is provided on an image plane IM. Light from the reduction plane OP passes through a cemented lens of lenses L21 and L22, a diaphragm AP, and a cemented lens of lenses L23 and L24 and forms an image on an image plane IM. The optical system MO illustrated in FIG. 7 provides the same size (1× magnification) and is telecentric on both the object side and the image side, but the magnification and the angle of view are not limited to those in this example. Although the optical system MO in FIG. 7 includes a plurality of lenses, the number and arrangement of the lenses are not limited to those shown, and another optical element such as a reflective surface may be included.

EXAMPLE 2

Figure 8:
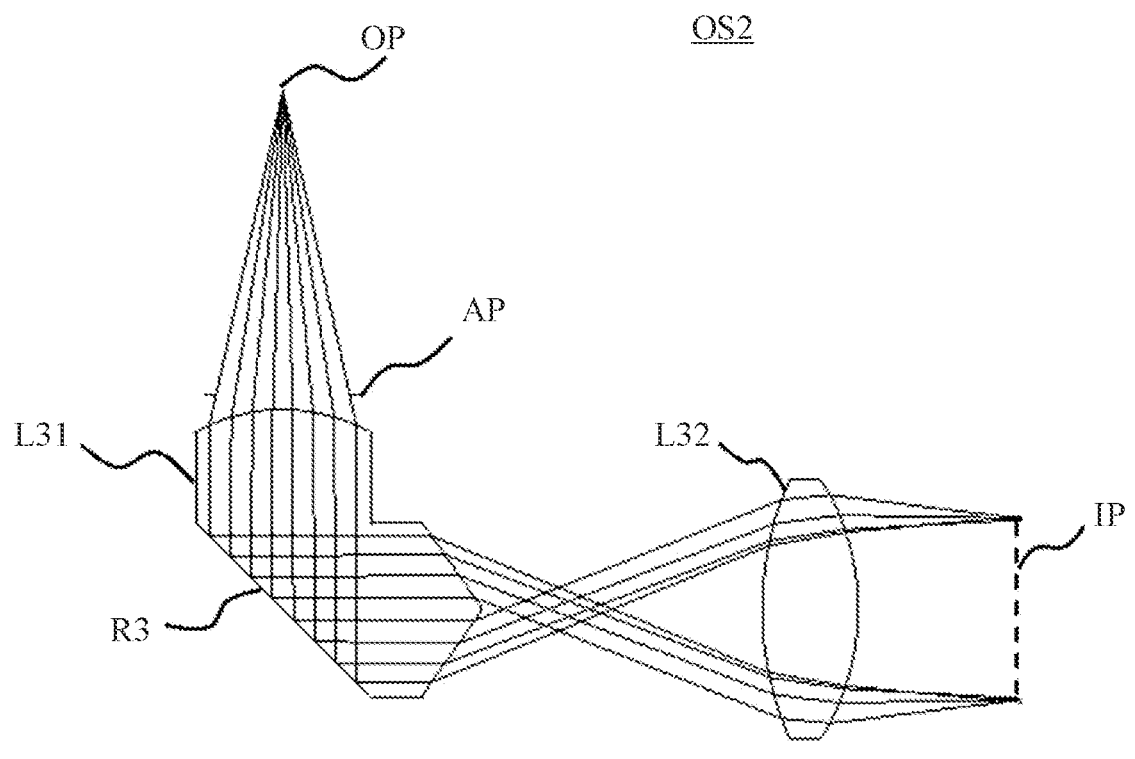
FIG. 8 is a sectional view of an optical system according to Example 2.

Referring now to FIG. 8, a description will be given of an optical system OS2 according to Example 2. FIG. 8 is a sectional view of the optical system OS2.

The optical system OS2 includes, in order from the reduction plane OP to the enlargement plane PP (refer to FIG. 1), a diaphragm AP, a lens L31 including a reflective surface R3, and a lens L32. In this embodiment, the lens L31 is an optical element having a conical surface. The lens L31 has an action of collimating the light from the reduction plane OP, an action of bending the optical path, and an action of converting a shape of the light beam into a ring shape. Light from lens L31 passes through lens L32 and forms a ring-shaped intermediate image IP. The ring-shaped intermediate image IP enters the enlargement plane PP, that is, the retina (fundus) in the eye. An exit surface of the lens L31 is a conical surface. The reflective surface R3 serves as a half mirror or a PBS. The angle (reflection angle) of the reflective surface R3 is not limited to that illustrated in FIG. 8. Integrating the action of collimating light, the action of bending the optical path, and the action of converting a shape of light into a ring shape is beneficial to improved arrangement accuracy, reduction in the number of components, and miniaturization. The exit surface of the lens L31 is a convex conical surface, but is not limited to this example, and may be a concave conical surface.

EXAMPLE 3

Figure 9:
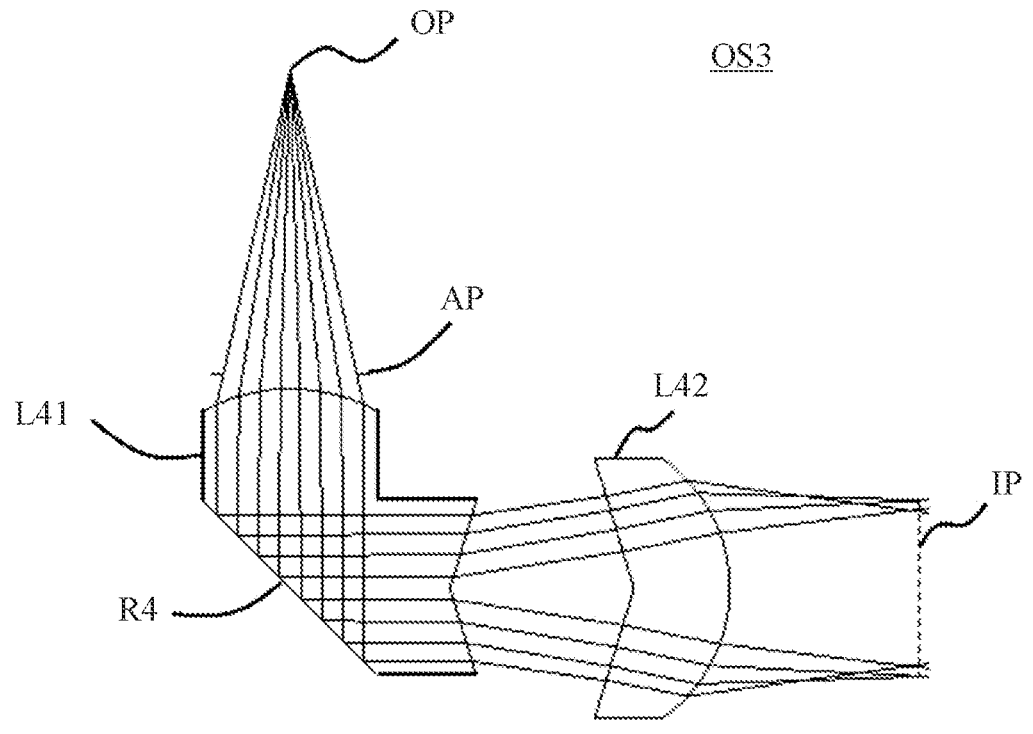
FIG. 9 is a sectional view of an optical system according to Example 3.

Referring now to FIG. 9, a description will be given of an optical system OS3 according to Example 3. FIG. 9 is a sectional view of the optical system OS3.

The optical system OS3 includes, in order from the reduction plane OP to the enlargement plane PP, a diaphragm AP, a lens L41 including a reflective surface R4, and a lens L42. In this embodiment, the lenses L41 and L42 are optical elements each having a conical surface. The lens L41 has an action of collimating the light from the reduction plane OP, an action of bending the optical path, and an action of converting a shape of the light beam into a ring shape. Light from the lens L41 passes through the lens L42 and forms a ring-shaped intermediate image IP. The ring-shaped intermediate image IP enters the enlargement plane PP, that is, the retina (fundus) in each eye. The exit surface of the lens L41 and the entrance surface of lens L42 are conical surfaces. The reflective surface R4 serves as a half-mirror or a PBS. The angle (reflection angle) of the reflective surface R4 is not limited to the angle illustrated in FIG. 8. Forming the exit surface of the lens L41 and the entrance surface of the lens L42 into conical surfaces can shorten the distance between the lenses L41 and L42 and is beneficial to miniaturization. In that case, the conical surfaces of the lenses L41 and L42 may be concave.

Numerical examples 1 to 4 corresponding to examples 1 to 3 will be illustrated below. Numerical example 1 indicates the optical system OS1 according to Example 1. Numerical example 2 indicates the optical system MO according to Example 1. Numerical example 3 indicates the optical system OS2 according to Example 2. Numerical example 4 indicates the optical system OS3 according to Example 3.

In each numerical embodiment, a surface number denotes a number i of a surface counted from the reduction plane side, R (mm) denotes a radius of curvature of an i-th surface, and D (mm) denotes a distance (on the optical axis) between an i-th surface and an (i+1)-th surface. Nd and vd respectively denote a refractive index and an Abbe number based on the d-line (587.6 nm) of a medium between the i-th surface and the (i+1)-th surface. The Abbe number vd is expressed by the following expression:

$$vd=(Nd-1)/(NF-NC)$$

where NF and NC are refractive indices based on the F-line (486.1 nm) and C-line (656.3 nm) of the medium between the i-th surface and the (i+1)-th surface.

The axicon lens is represented by the following equation:

$$z=Cr$$

where C is an aspheric coefficient, and r is expressed by the following equation:

$$r=\sqrt{(x^2+y^2)}$$

Here, the optical axis is set to a z-axis, and a direction from the reduction plane to the enlargement plane is set positive (+z direction). An axis orthogonal to the z-axis is a y-axis, and an axis orthogonal to the z-axis and the y-axis is set to the x-axis.

NUMERICAL EXAMPLE 1

| Surface No. | | R | D | Nd | vd |
|---|---|---|---|---|---|
| 1 | OP | ∞ | −40.00 | 1.000 | |
| 2 | L11 | ∞ | −5.00 | 1.521 | 64.14 |
| 3 | | 23.000 | −15.00 | 1.000 | |
| 4 | R1 | ∞ | 15.00 | 1.000 | |
| 5 | AP | ∞ | 30.00 | 1.000 | |
| 6 | L12 | ∞ | 5.00 | 1.462 | 67.80 |
| 7 | | ∞ | 13.00 | 1.000 | |
| 8 | L13 | 22.200 | 12.00 | 1.521 | 64.14 |
| 9 | | ∞ | 25.00 | 1.000 | |
| 10 | | ∞ | 500.00 | 1.000 | |
| 11 | PP | ∞ | | | |
| 6th Surface | | | | | |
| C = −0.5 | | | | | |

NUMERICAL EXAMPLE 2

| Surface No. | | R | D | Nd | vd |
|---|---|---|---|---|---|
| 1 | OP | ∞ | 12.00 | 1.000 | |
| 2 | L21 | 9.832 | 4.00 | 1.562 | 56.36 |
| 3 | L22 | −6.017 | 1.00 | 1.792 | 40.93 |
| 4 | | −13.237 | 11.18 | 1.000 | |
| 5 | AP | ∞ | 11.18 | 1.000 | |
| 6 | L23 | 13.656 | 1.00 | 1.792 | 40.93 |
| 7 | L24 | 6.065 | 4.00 | 1.562 | 56.36 |
| 8 | | −9.594 | 12.00 | 1.000 | |
| 9 | IM | ∞ | | | |

NUMERICAL EXAMPLE 3

| Surface No. | | R | D | Nd | vd |
|---|---|---|---|---|---|
| 1 | OP | ∞ | −38.00 | 1.000 | |

-continued

| Surface No. | | R | D | Nd | vd |
|---|---|---|---|---|---|
| 2 | AP | ∞ | −2.00 | 1.000 | |
| 3 | L31 | −22.700 | −25.00 | 1.462 | 67.80 |
| 4 | R3 | ∞ | 25.00 | 1.462 | 67.80 |
| 5 | | ∞ | 35.00 | 1.000 | |
| 6 | L32 | 40.000 | 12.00 | 1.521 | 64.14 |
| 7 | | −30.500 | 25.00 | 1.000 | |
| 8 | | ∞ | 400.00 | 1.000 | |
| 9 | PP | ∞ | | | |
| 5th Surface | | | | | |
| C = −0.7 | | | | | |

NUMERICAL EXAMPLE 4

| Surface No. | | R | D | Nd | vd |
|---|---|---|---|---|---|
| 1 | OP | ∞ | −38.00 | 1.000 | |
| 2 | AP | ∞ | −2.00 | 1.000 | |
| 3 | L41 | −22.700 | −25.00 | 1.462 | 67.80 |
| 4 | R4 | ∞ | 20.00 | 1.462 | 67.80 |
| 5 | | ∞ | 23.00 | 1.000 | |
| 6 | L42 | ∞ | 12.00 | 1.462 | 67.80 |
| 7 | | −20.000 | 25.00 | 1.000 | |
| 8 | | ∞ | 500.00 | 1.000 | |
| 9 | PP | ∞ | | | |
| 5th Surface | | | | | |
| C = 0.3 | | | | | |
| 6th Surface | | | | | |
| C = −0.3 | | | | | |

Table 1 below summarizes values of inequalities (1) and (2) in the optical systems OS1, OS2 and OS3 according to numerical examples 1, 3, and 4.

TABLE 1

| | OS1 | OS2 | OS3 |
|---|---|---|---|
| Fo | 4.59 | 3.83 | 3.83 |
| β | 0.97 | 0.75 | 1.00 |
| L | 500.00 | 400.00 | 500.00 |
| Fo × β | 4.45 | 2.87 | 3.81 |
| L × B/(2 × Fo) | 52.81 | 39.03 | 64.92 |

Inspection Apparatus

Figure 10:
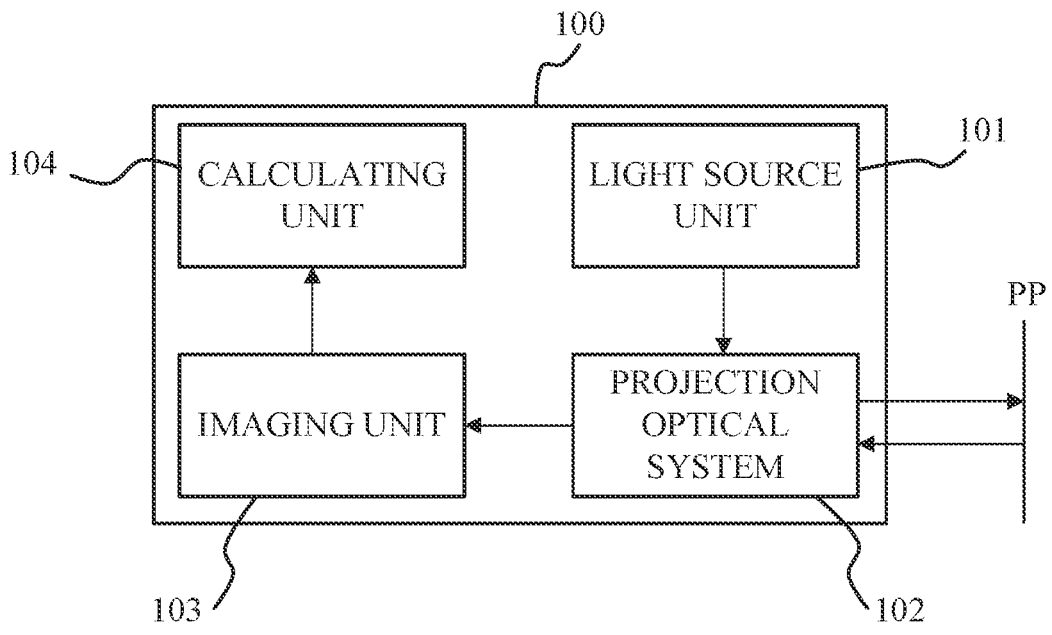
FIG. 10 is a block diagram of an inspection apparatus according to each example.

Referring now to FIG. 10, a description will be given of an inspection apparatus (fixation measurement apparatus) 100. FIG. 10 is a block diagram of the inspection apparatus 100. The inspection apparatus 100 identifies the fovea in the retina and inspects a position where the subject is viewing (fixation state) using the image sensor SS to detect changes in polarization between light incident on the retina in the eye of the subject and light reflected from the retina.

The inspection apparatus 100 includes a light source unit 101, a projection optical system 102, an imaging unit (imaging optical system) 103, and a calculating unit 104. The light source unit 101 has a light source, such as a laser diode, and emits light toward the projection optical system 102. The projection optical system 102 corresponds to any one of the optical systems OS1 to OS3 according to Examples 1 to 3. The imaging unit 103 receives light reflected from the retina (fundus) in the eye on the enlargement plane PP. The imaging unit 103 acquires information on polarization of light incident on the retina and light reflected from the retina. The calculating unit 104 has an image processing technology that separates the information reflected from the retinas in both eyes so that each piece of information corresponds to each eye.

Figure 11:
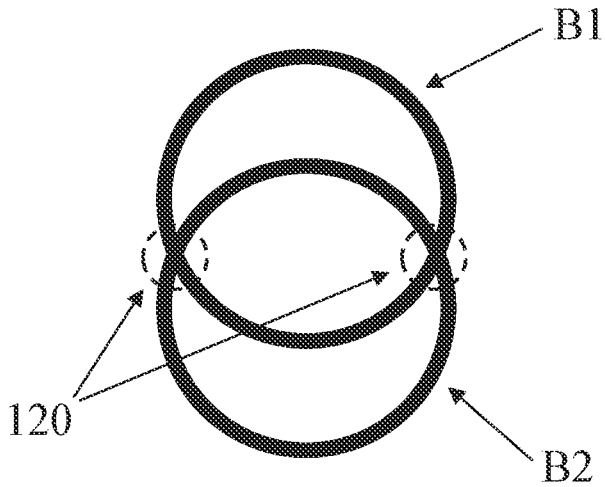
FIG. 11 illustrates a state on an imaging plane according to each example.

FIG. 11 illustrates the state on the imaging plane of the reflected lights B1 and B2 from both eyes of the subject viewed from the optical path direction. As illustrated in FIG. 11, the reflected lights B1 and B2 from the retinas are received in a partially overlapping state. In the calculation by the calculating unit 104, signals corresponding to portions 120 that overlap each other are discarded or ignored for inspection, or supplemented by estimating from the continuity of the ring, so that information on the reflected lights B1 and B2, that is, the left-eye information and the right-eye information can be separated. Eye information other than fixation may be detected from the positions of the rings, the distance between the rings, the radius, the shape, and the like. In a case where the reflected lights B1 and B2 overlap each other almost perfectly and the complement is difficult, a method of separating the left-eye information and the right-eye information using a phase difference of each light may be used. While FIG. 11 assumes ring-shaped reflected light, a different pattern may be assumed and acquired based on the aberration of the optical system in the inspection apparatus, the pattern shape of the intermediate image, and the like. In that case, the left-eye information and the right-eye information can be also separated by ignoring and complementing the signals of the overlap portions 120 based on the pattern shape.

Each example can provide an optical system and an inspection apparatus each of which is small and has a simple configuration by directly imaging (receiving) the sectional area of the reflected light from the retina, because it is unnecessary to optically separate the lights reflected from both eyes.

While the disclosure has been described with reference to embodiments, it is to be understood that the disclosure is not limited to the disclosed embodiments. The scope of the following claims is to be accorded the broadest interpretation so as to encompass all such modifications and equivalent structures and functions.

This application claims the benefit of Japanese Patent Application No. 2022-023869, filed on Feb. 18, 2022, which is hereby incorporated by reference herein in its entirety.

What is claimed is:

1. An optical system comprising a first optical element having a conical surface, wherein the first optical element is configured to guide light from a light source to a first target and a second target, and to guide first reflected light from the first target and second reflected light from the second target to an image sensor, wherein an intermediate image is formed between the first optical element and each of the first target and the second target, and wherein the first reflected light and the second reflected light are guided to an imaging plane of the image sensor such that at least part of the first reflected light and part of the second reflected light overlap each other on the imaging plane.

2. The optical system according to claim 1, further comprising:

a projection optical system configured to guide the light onto the first target and the second target; and an imaging optical system configured to guide the first reflected light and the second reflected light onto the image sensor, wherein the first optical element constitutes a part of the projection optical system and a part of the imaging optical system.

3. The optical system according to claim 2, wherein the imaging optical system includes a light shielding unit configured to shield part of at least one of the first reflected light and the second reflected light.

4. The optical system according to claim 2, wherein the imaging optical system includes a screen configured to diffuse the first reflected light and the second reflected light while maintaining a polarization state of each of the first reflected light and the second reflected light.

5. The optical system according to claim 4, wherein the imaging optical system includes a second optical element configured to guide light from the screen to the image sensor.

6. The optical system according to claim 1, further comprising an optical diaphragm, wherein the optical diaphragm has a rectangular or elliptical aperture, and wherein a longitudinal direction of the aperture is a direction from the first target to the second target.

7. The optical system according to claim 6, wherein the following inequality is satisfied:

$$1.8 \le Fo \times \beta \le 7.0$$

where Fo is a target-side effective F-number in the longitudinal direction, and $\beta$ is a magnification.

8. The optical system according to claim 6, wherein the following inequality is satisfied:

$$20 \le L \times \beta / (2 \times Fo)$$

where Fo is a target-side effective F-number in the longitudinal direction of the optical system, $\beta$ is a magnification, and L is the shortest distance from the intermediate image to a plane where the first target and second target are located.

9. An inspection apparatus comprising:

an image sensor; and an optical system, wherein the optical system includes a first optical element having a conical surface, wherein the first optical element is configured to guide light from a light source to a first target and a second target, and to guide first reflected light from the first target and second reflected light from the second target to an image sensor, wherein an intermediate image is formed between the first optical element and each of the first target and the second target, and wherein the first reflected light and the second reflected light are guided to an imaging plane of the image sensor such that part of the first reflected light and part of the second reflected light overlap each other on the imaging plane.

10. The inspection apparatus according to claim 9, further comprising a calculating unit configured to separate first image data corresponding to the first reflected light and output from the image sensor and second image data corresponding to the second reflected light and output from the image sensor.

11. The inspection apparatus according to claim 10, wherein the calculating unit separates the first image data and the second image data based on a polarization state of each of the first reflected light and the second reflected light.

12. The inspection apparatus according to claim 9, wherein the image sensor receives the first reflected light and the second reflected light from the first target and the second target disposed at positions conjugate with the intermediate image.

13. The inspection apparatus according to claim 9, wherein the first target and the second target are a left eyeball and a right eyeball, respectively, and wherein the image sensor simultaneously receives the first reflected light and the second reflected light.

14. The inspection apparatus according to claim 9, further comprising a calculating unit, wherein the first target and the second target are a left eyeball and a right eyeball, respectively, and wherein the calculating unit detects a fixation state of each of the left eyeball and the right eyeball.

* * * * *